United States Patent
Al Ahmad (10) Patent No.: US 9,523,669 B2
(45) Date of Patent: Dec. 20, 2016

(54) APPARATUS AND METHOD FOR VIRUS DETECTION

(71) Applicant: United Arab Emirates University, Al-Ain (AE)

(72) Inventor: Mahmoud Al Ahmad, Al-Ain (AE)

(73) Assignee: United Arab Emirates University, Al-Ain (AE)

( * ) Notice: Subject to any disclaimer, the term of this patent is extended or adjusted under 35 U.S.C. 154(b) by 204 days.

(21) Appl. No.: 14/050,485

(22) Filed: Oct. 10, 2013

(65) Prior Publication Data

US 2015/0104783 A1    Apr. 16, 2015

(51) Int. Cl.
G01N 33/48      (2006.01)
G01N 33/50      (2006.01)
G01N 33/487     (2006.01)

(52) U.S. Cl.
CPC ...... *G01N 33/487* (2013.01); *G01N 33/48707* (2013.01); *Y10S 977/72* (2013.01); *Y10S 977/73* (2013.01); *Y10S 977/742* (2013.01); *Y10S 977/746* (2013.01); *Y10S 977/784* (2013.01); *Y10S 977/802* (2013.01); *Y10S 977/806* (2013.01)

(58) Field of Classification Search
None
See application file for complete search history.

(56) References Cited

FOREIGN PATENT DOCUMENTS

WO      02/080361 A1    10/2002
WO      2009/048695 A2   4/2009

OTHER PUBLICATIONS

Patolsky et al. Electrical detection of single viruses. PNAS, 2004, vol. 101, pp. 14017-14022.*
Chen et al. An investigation of the mechanisms of electronic sensing of protein adsorption on carbon nanotube devices. Journal of the American Chemical Society, 2004, vol. 126, pp. 1563-1568.*
Tan et al. Controllable fabrication and electrical performance of single crystalline Cu2O nanowires with high aspect ratios. Nano Letters, 2007, vol. 7, pp. 3723-3728.*
Lieber CM. Integrated nanoscale nanowire correlated electronic nanosensing (INNOCENT), Jun. 20, 2006, 27 pages.*
Elsheakh, D. et al. "Novel rapid detection of different viruses in blood using microimmuno-sensor." In: 2013 7th European Conference on Antennas and Propagation (EuCAP), Apr. 8-12, 2013, Gothenburg, pp. 1128-1131. IEEE.
Lonappan, A. "Novel method of detecting H1N1 using microwaves." Journal of Biomedical Science and Engineering, 2012, vol. 5, pp. 476-479.
Gupta, A. et al. "Single virus particle mass detection using microresonators with nanoscale thickness." Applied Physics Letters, 2004, vol. 84, No. 11, pp. 1976-1978.

(Continued)

*Primary Examiner* — Russell S Negin
(74) *Attorney, Agent, or Firm* — Katten Muchin; Rosenman LLP (57) ABSTRACT

Embodiments of the present invention relate to a method comprising obtaining a radio frequency response of a lab-on-chip based resonator with virus deposited within a recess of the resonator, determining at least one parameter of the radio frequency response and identifying a type of the virus or a group to which the virus belongs based on the at least one parameter.

16 Claims, 8 Drawing Sheets

(56) References Cited

OTHER PUBLICATIONS

Barton, R.A. et al. "Fabrication of a nanomechanical mass sensor containing a nanofluidic channel" Nano Letters, 2010, vol. 10, pp. 2058-2063.
Cui, Yan et al. "A simple, tunable, and highly sensitive radio-frequency sensor." Applied Physics Letters, Aug. 8, 2013, vol. 103, pp. 062906-(1-3).
Al Ahmad, M. et al. "RF Microalgal lipid content characterization." Scientific Reports, May 29, 2014, vol. 4, pp. 5108-(1-6).
International Search Report for International Application No. PCT/IB2014/065180 with a mailing date of Mar. 30, 2015.
Written Opinion of the International Searching Authority for International Application No. PCT/IB2014/065180 with a mailing date of Mar. 30, 2015.

\* cited by examiner

APPARATUS AND METHOD FOR VIRUS DETECTION

TECHNICAL FIELD

This invention relates to apparatus, systems and methods for virus detection. In particular, but not exclusively, embodiments of this invention relate to uses of nanotechnology and radio frequency techniques in identifying a type of virus.

BACKGROUND

It is widely known that many diseases are caused by viruses. It is therefore important to be able to detect viruses and identify a detected virus to be a particular type of virus as quickly as possible, since it could enable diagnosis at the earliest stages of replication within the host's system, and allow speedy medical decision-making. Moreover, accurate quantification of viruses is very essential for the development of their corresponding vaccines and it is desirable to be able to distinguish between different kinds of viruses presented in a sample.

Many studies are being conducted on developing sensing mechanisms that help speed up virus detection and identification. Most of the existing virus screening and quantifying techniques suffer from limitations, such as the need for extensive sample preparation and steps including viral isolation, extraction, and purification, or from the limitations that they are very costly and time consuming to carry out.

SUMMARY OF THE INVENTION

A first aspect of the present invention provides a method, comprising: obtaining a radio frequency response of a lab-on-chip based resonator with virus deposited within a recess of the resonator, determining at least one parameter of the radio frequency response, and identifying a type of the virus or a group to which the virus belongs based on the at least one parameter.

In one embodiment, said at least one parameter is an amplitude or a change of amplitude at a resonance frequency of the resonator with the virus deposited therein.

In one embodiment, the method further comprises measuring said at least one parameter of a radio frequency response when a different types of virus is deposited within the resonator, composing a lookup table containing at least said two types of viruses and their respective frequency response measurements.

In one embodiment, the lab-on-chip based resonator comprises nanotubes, and said depositing virus within the recess of the resonator comprises depositing virus between the gaps of the nanotubes.

In one embodiment, the virus is mixed with functionalized nanoparticles when being deposited within a recess of the resonator.

In one embodiment, the nanoparticles are antibodies and/or quantum dots.

In one embodiment, the said obtaining a radio frequency response of the resonator is performed by a Vector Network Analyser (VNA), which is configured to collect a set of scattering parameter measurements to determine the resonance frequency and a signal amplitude at the resonance frequency.

In one embodiment, said at least one parameter comprises at least one of: a resonance frequency, a change in resonance frequency, a phase at a particular frequency, and a phase shift at a particular frequency of the frequency response.

In one embodiment, said obtaining a radio frequency response is performed at a first temperature, and said determining determines said at least one parameter of the radio frequency response obtained at the first temperature, wherein the method further comprises obtaining, at a second temperature, a radio frequency response of the resonator with the virus deposited within the recess of the resonator, determining a second parameter of the radio frequency response obtained at the second temperature, and wherein said identifying a type of the virus or a group to which the virus belongs is performed based on a comparison between said first parameter and said second parameter.

In one embodiment, said the first temperature is 37° C., and the second temperature is 47° C.

In one embodiment, the method comprises identifying a type of the virus to be HIV if the first parameter and the second parameter are substantially identical, wherein the first parameter and the second parameter are both a magnitude of the frequency response at the resonance frequency.

In one embodiment, said determining a signal amplitude at a resonant frequency of the resonator at the first and the second temperatures is performed by a Vector Network Analyser, which is configured to collect a set of scattering parameter measurements to determine the resonant frequency and the signal amplitude.

A second aspect of the present invention provides an apparatus or a system, comprising: a device for obtaining a radio frequency response of a lab-on-chip based resonator with virus deposited within a recess of the resonator, a device for determining at least one parameter of the radio frequency response, at least one processor and at least one memory, causing the apparatus or the system to identify a type of the virus or a group to which the virus belongs based on said at least one parameter of the radio frequency response.

In one embodiment, said device for determining at least one parameter is configured to determine a magnitude or a change of magnitude at a resonance frequency of the resonator with the virus deposited therein.

In one embodiment, said device for obtaining a radio frequency response of the resonator is a Vector Network Analyser (VNA).

In one embodiment, wherein said device for obtaining a radio frequency response is configured to obtain a radio frequency response at both a first temperature and a second temperature, and wherein said device for determining at least one parameter is configured to determine a first parameter of the radio frequency response obtained at the first temperature and to determine a second parameter of the radio frequency response obtained at the second temperature, wherein said at least one processor and said at least one memory are configured to cause the apparatus or system to identify a type of the virus or a group to which the virus belongs based on a comparison between said first parameter and said second parameter.

In one embodiment, wherein the first temperature is 37° C., and the second temperature is 47° C.

In one embodiment, the apparatus or system comprises identifying a type of the virus to be HIV if the first parameter and the second parameter are substantially identical.

In one embodiment, said at least one parameter comprises at least one of: a resonance frequency, a change in resonance frequency, a phase at a particular frequency, and a phase shift at a particular frequency of the frequency response.

In one embodiment, said at least one processor and at least one memory are configured to cause the apparatus to identify a type of the virus or a group to which the virus belongs based on said at least one parameter of the radio frequency response and data stored in the memory.

BRIEF DESCRIPTION OF THE DRAWINGS

Embodiments of the present invention will now be described by way of example with reference to the accompanying drawings.

DETAILED DESCRIPTION

Embodiments of this invention provide a method for comprising: obtaining a radio frequency response of a lab-on-chip based resonator with virus deposited within a recess of the resonator, determining at least one parameter of the radio frequency response, and identifying a type of the virus or a group to which the virus belongs based on the at least one parameter.

Figures 1, 2, 3:
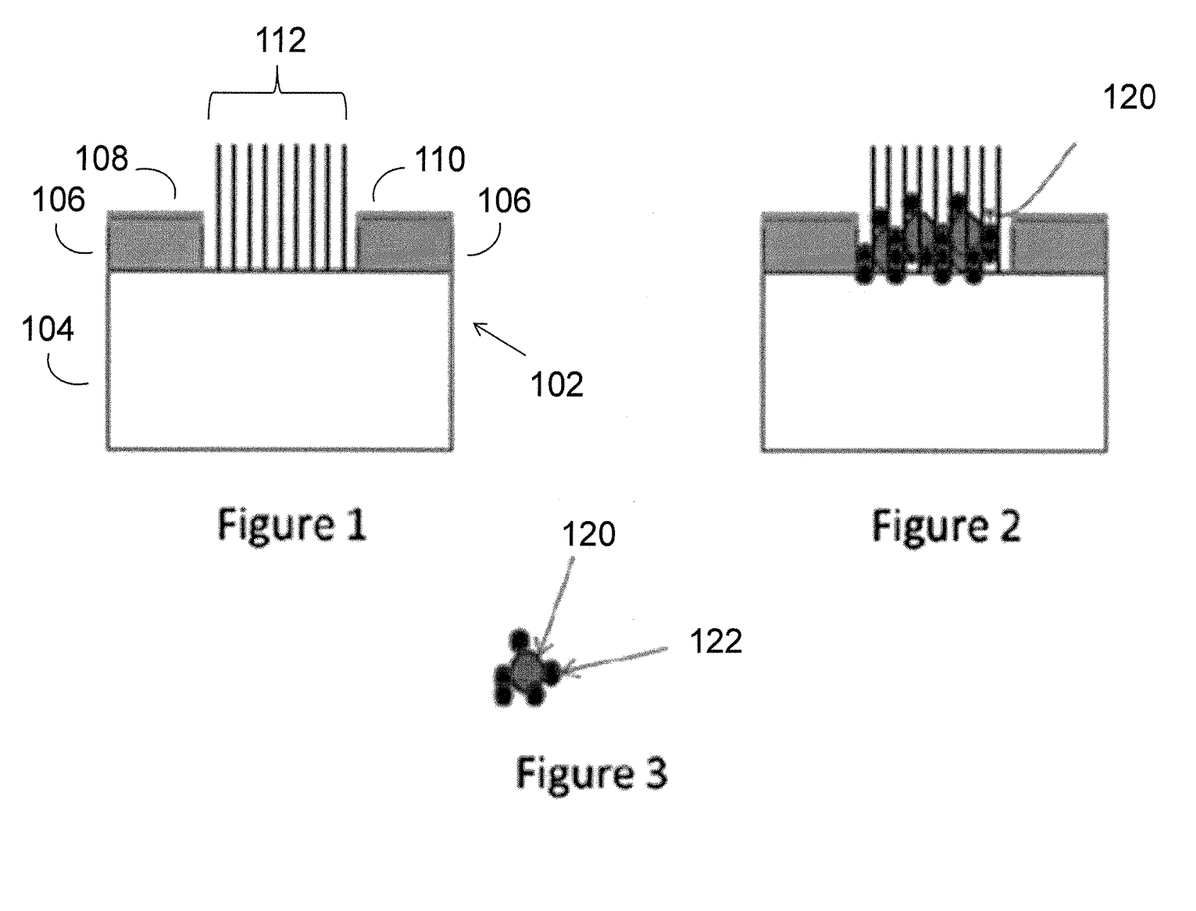
FIG. 1 shows a cross-sectional view of a nano-tube based resonator used in a first embodiment of the invention.
FIG. 2 shows a cross-sectional view of the nano-tube based resonator used in the first embodiment of the invention with virus deposited therein.
FIG. 3 shows functionalized nanoparticles (or quantum dots) and virus sticking to them.

FIG. 1 shows a nano-tube based resonator 102 implemented on a lab-on-a-chip (LOC) used in a first embodiment of the invention. A lab-on-a-chip is a device that integrates one or several laboratory functions on a single chip with a size in the order of millimeters to a few square centimeters. The lab-on-a-chip used for this embodiment comprises a gap or indentation with small dimensions, e.g. in the range of several micros, on the lab-on-a-chip device and a mechanical resonator comprising an array of vertical nanotubes placed within the gap.

In the embodiment shown in FIG. 1, the apparatus 102 comprises a substrate 104, dielectric materials 106, input electrode metallization 108, output electrode metallization 110 and nanotubes array 112.

The resonator 102 behaves as a band pass filter to RF signals propagating through it and has a certain quality factor (Q factor). When RF signals propagate from input 108 to output 110, the resonator rejects or attenuates RF signals with frequencies not matching its mechanical resonance frequency. Therefore, most or all of these RF signals are reflected back and few of them at or very close to the resonance frequency of resonator 102 are transmitted through the nanotubes array. At a RF signal frequency that matches the mechanical resonance of the resonator 102, a substantial proportion of power is transmitted through although a small proportion of power is still reflected.

The nano-tubes array 112 may be isolated from the substrate by a dielectric layer (not shown in the drawings) in case that the tubes are metallic or made of semiconductor. The nano-tubes array 102 may be functionalized so that it provides an enhanced stickiness to virus and can more easily capture virus. The distances between the nano-tubes are large enough to host nanoparticles between them.

The mechanical resonance frequency of the nano-tubes array 112 and overall frequency performance of the device 102 depends on a number of design parameters: materials, diameter and length of the nano-tubes, distance between the nano-tubes and the properties of the dielectric materials that are used to decorate the array, and also the density of the nano-tubes in the array.

FIG. 2 illustrates the nano-tube based resonator 102 with virus specimen in a liquid form deposited among the nano-tubes. The liquid specimen may be mixed with functionalized nano-particles or quantum dots, which could be magnetic, metallic or dielectric. FIG. 2 shows an arrangement ready for measurements. As will be explained later, the deposition of virus on the lab-on-chip device will change the frequency response characteristics of the device.

FIG. 3 illustrates functionalized nano-particles (or quantum dots) 120 and virions (virus particles) 122 sticking onto them. The functionalized nano-particles (or quantum dots) 120 are used to provide a carrier for the virions 122 and to increase sensitivity of the measurements.

The virions 122 stick onto the nano-particles (or quantum dots) 120 more easily than directly onto nano-tubes. The nano-particles 120 may be coated with special materials to capture the virions 122 and make the virus 122 stick to them.

FIG. 4 shows a cavity/gap coupling resonator 302 implemented on a lab-on-a-chip device. The resonator 302 comprises a substrate 304, dielectric materials 306, input electrode metallization 308, output electrode metallization 310, a gap/cavity 314. The gap 314 behaves like a capacitance and the electrodes 308 and 310 behave like inductors to RF signals. Thus the combination acts as an L-C resonance circuit to RF signals and resonates at its resonance frequency.

The resonator 302 has a certain quality factor (Q factor) and behaves like a band pass filter to RF signals propagating through it. When RF signals propagate from input 308 to output 310, the resonator rejects or attenuates RF signals with frequencies not matching its mechanical resonance frequency. Therefore, most or all of these RF signals are reflected back and few of them substantially at and near the resonance frequency are transmitted through the resonator 302. At a frequency that matches the resonance frequency of the resonator 302, a substantial proportion of power is transmitted through although a small proportion of power is still reflected.

The resonance frequency and overall frequency performance of the resonator 302 depends on a number of parameters: dietetic material or other materials that are deposited above the substrate, distance between the input and output, dimensions of the gap, etc.

FIG. 5 shows that virus specimen with nanoparticles (or quantum dots) is deposited within the gap/cavity, and that the total arrangement is ready for measurements.

The nanoparticles are dielectric materials and their insertion will change the effective dielectric constant of the cavity, the air gap capacitance and thus the resonant frequency and frequency response characteristics as a consequence of changing the gap capacitance.

Figure 6A:
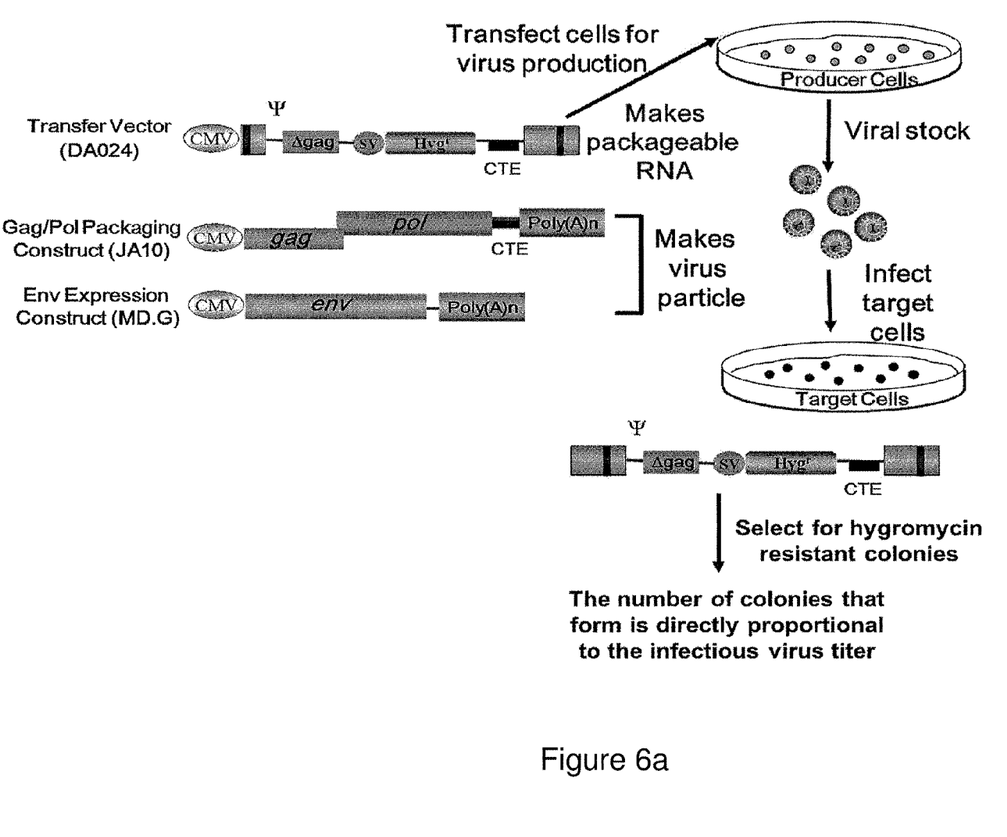
FIGS. 6a and 6b show a system for laboratory production of a virus of a certain amount.
Figure 6B:
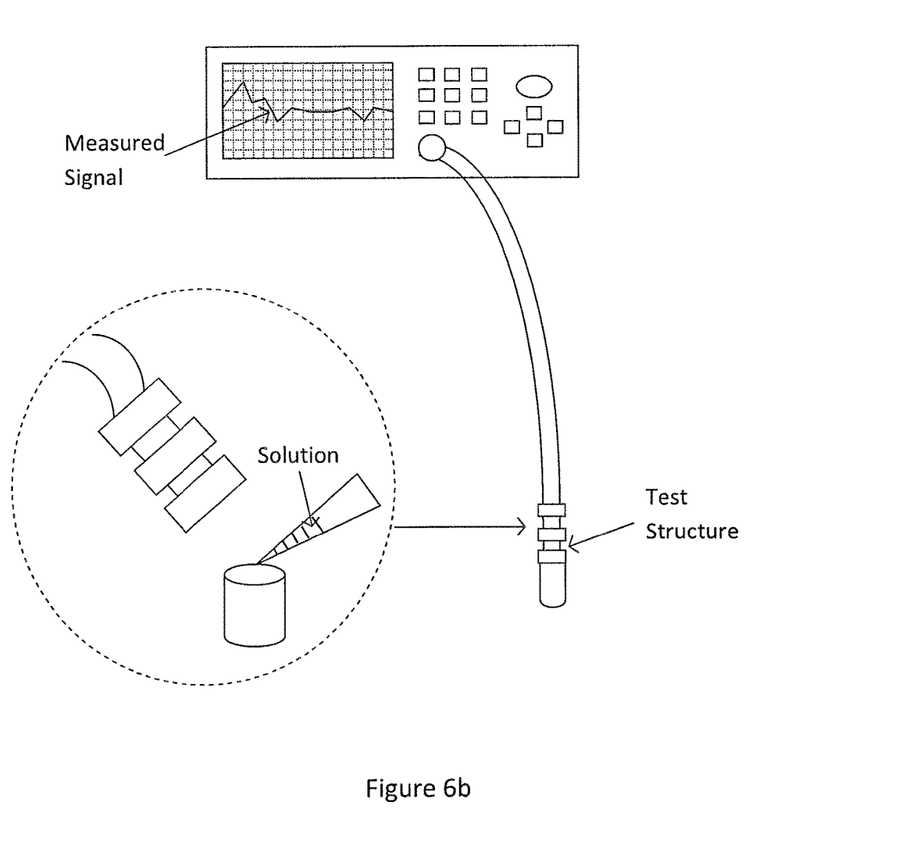

FIG. 6a illustrates a method for ensuring that equal amounts of different types of viral particles are used for radio frequency signature analysis. It illustrates that four different retroviral particles were produced employing the principle of genetic trans complementation assay and was used for studying HIV, FIV, MPMV, and MMTV replication. These trans complementation assays consist of a packaging construct, JA10 (MMTV), TR301 (MPMV), MB22 (FIV), and CMVΔR8.2 (HIV) expressing respective viral gag/pol genes, and therefore resulting in the production of viral particles, which are capable of encapsulating respective retroviral RNAs. The source of the packageable RNA is provided by DA024 (MMTV), SJ2 (MPMV) TR394 (FIV), and MB58 (HIV) transfer vectors. These transfer vectors express hygromycin resistance as a marker gene, which monitors the successful retroviral particle production by quantitatively analyzing the transduced target cells with this marker gene (FIG. 6a). The number of Hygromycin-resistant ($Hyg^r$) colonies obtained should be directly proportional to the amount of viral particles produced and RNA that is packaged into the virus (FIG. 6a). An envelope expression plasmid (MD.G) based on vesicular stomatitis virus envelope G (VSV-G) was used to pseudotype different retroviral particle. Briefly, in these assays, the three plasmids (for example JA10+DA24+MD.G in the case of MMTV) were co-transfected into 293T producer cells, which generated virus particles containing the encapsulated RNA (FIG. 6*a*).

These virus particles were used to monitor the specific radio frequency signatures for these retroviruses. In addition, these viral particles were also used to infect target cells resulting in the transduction of these cells with the marker gene present on the packaged RNA, thus allowing for monitoring the propagation of the transfer vector RNA, which could only take place if the virus particles are efficiently produced. The rationale behind pseudotyping different retroviral particles by a common VSV envelope glycoprotein (Env-gp) is based on the fact that all of these retroviral particles (HIV, FIV, MMTV, and MPMV) will be decorated by the similar Env-gp.

To ensure that equal amounts of viral particles are used for radio frequency signature analysis, each transfection was carried out in the presence of an independent DNA, pGL3 Control vector, expressing the luciferase gene. This allows monitoring the transfection efficiencies in our cell cultures as described previously. The amount of culture supernatant (virus particle) used for radio frequency signature analysis for each retrovirus was determined by following a normalization with the transfection efficiencies using the relative light units/μg of protein (RLU).

In one embodiment, each kind of virus is suspended into Dulbecco's Modified Eagle Medium (DMEM), and each mixture is exposed to a radio frequency signal with a power of 10 dBm and with a sweep from 10 MHz up to 13.6 GHz using the measurements setup which is shown in FIG. 6*b*.

In the embodiment shown in FIG. 6*b*, a Vector Network Analyzer (VNA) is used to take the measurements. The VNA is able to take high frequency scattering parameters measurements of a filled coaxial based resonator structure with appropriate medium at defined resonance frequency band to characterize viruses.

A virus specimen is loaded into a hosting RF coaxial resonator structure. The self-resonance frequency of the coaxial cables is set to be above 30 GHz, and will not affect the measurements in the aforementioned frequency range, namely 10 MHz to 13.6 GHz. The system is calibrated using SLOT transmission line techniques for the network analyzer to ensure that the measurements are representations of the mixture solution, but not anything else. A typical calibration will move the measurement reference planes to the end of the test cables. Therefore, it will exclude the effect of losses and phase shifts that could add noise to the measured signal.

FIG. 7 illustrates frequency response characteristics of four types of viruses: FIV, MPMV, MMTV and HIV (corresponding to V1, V2, V3 and V4 in FIG. 7 respectively) at different temperatures. In the test, each kind of virus was suspended into Dulbecco's Modified Eagle Medium (DMEM) before deposited on the lab-on-chip device. A medium response (corresponding to M in FIG. 7), i.e. a response of the DMEM medium deposited on the lab-on-chip alone without any virus, is also measured for comparison with the responses for the viruses. For these four types of viruses, an equal amount of viral particles have been used for their radio frequency signature analysis.

As illustrated in FIGS. 7*a*, 7*b* and 7*c*, frequency response profiles of the viruses generally follow the medium frequency behavior, with an expected deviation in magnitude at certain frequency bands, such as the resonance bandwidth. At this frequency band, the viruses are susceptible to RF polarization which depends on the compositions of the virus itself and its interaction with the medium polarity and/or ionic strength. As the viruses are of small sizes which are in the range of several tens of nanometers (up to 300 nm) in diameter, the virions could be modeled as nanoparticles, and when they are subjected to propagation of RF field they will get polarized due to the induced charging effect as in the case of nanoparticles. This is because as the signal frequency increases from a small level and signal wavelength becomes smaller. When the RF signal wavelength becomes comparable with the size of virions, the RF signal could modulate electrical charge distribution in the virus which in turn can create a polarizing effect on the virions, cause the virus particles to agitate and trigger impact ionization, which enables detection and identification of virus. The RF field propagating through the viruses will be altered in magnitude and phase depending on the virus properties, such as dielectric constant and electrical resistive losses. However, the extent of alteration to magnitude and phase is frequency dependent and is different to signals at different frequencies. At the resonance frequency, the response exhibits a purely resistive behavior. Thus, the viruses could change the frequency response of the lab-on-chip under test, which in turn can be utilized for identification of virus type based on this amount of change.

FIG. 7*a* shows that the RF response at 7° C. of each type of virus follows the medium response except at the resonance frequency around 12 GHz, where the RF responses of the four types of viruses clearly differ in their magnitudes. The response signal corresponding to the FIV (V1 in FIG. 7) is found to be close to the DMEM medium response behavior (M in FIG. 7) with reduction of magnitude of 0.3 dB at the resonance frequency, while the signals corresponding to MPMV and MMTV (V2 and V3 in FIG. 7 respectively) show a reduction of 2 and 2.4 dB, respectively. On the other hand, the HIV corresponding signal exhibits increment of 0.75 dB at the resonance frequency.

FIGS. 7*b* and 7*c* shows the frequency responses of these four types of viruses at 37° C. and 47° C. respectively. FIG. 7*d* shows a comparison of signal magnitudes at different temperatures for each of the four types of viruses. It shows that when the temperature increases from 37° C. to 47° C. the HIV associated signals do not change with the increase in temperature. However the other three types of viruses all have a more noticeable change in their signal magnitudes. Thus this approach can be used to detect a number of types of viruses without the need for labeling or biomarker. This also could provide a roadmap for the identification of viruses as well as molecular target candidates of other biological types.

Initially at 7° C. and as has been discussed, some virions exhibit negative differential DC resistance (MMTV, MPMV and FIV) and other exhibits positive differential DC resistance (HIV). As temperature increases, the liquid sample containing virus becomes less conductive, because the thermal vibrations in the lattice increase which causes more electron scattering and more collisions between electrons take place, slowing down flow of electrons. Consequently the rate of electric energy transfer by heating increases along with the electrical resistance causing the magnitude of the $S_{11}$ parameter in the S-parameters measured by the VNA to shift up.

In one embodiment, the frequency responses can be used to classify viruses. Viruses are classified based on their morphology, capsid and nucleic acid. Both MMTV and MPMV are categorized as beta retroviruses and this explains their close frequency behaviors. Similarly, FIV and HIV belong to the lentivirus group, and their frequency responses are close to each other. The capsid surrounds the virus and it is composed of a finite number of proteins. The lipid bilayer has an average thickness of about 5 nm, with a typical dielectric constant of 2. The change in $S_{11}$ parameter (one of the S parameters measured by the VNA) level is due to the associated intrinsic DC differential resistance of the virus itself. The increment in $S_{11}$ parameter is interpreted as the HIV virus introducing losses which are added to the mixture, thus increasing the effective total DC resistance, causing the level to be shifted up by 0.75 dB. Hence the virus is considered as a lossy material that exhibits certain loss dispersion over frequency. On the other side, the decrement in $S_{11}$ parameter can be attributed to viruses (MMTV and MPMV) exhibiting negative DC resistance. This will in turn reduce the total effective resistance of the mixture by subtracting the DMEM medium losses, thus causing the level to be shifted downward. Such a strategy streamlined the interpretation of the results in terms of specific radio frequency signatures for these different types of viruses, which could then be attributed solely to the specific nature of respective viral particles not due to the presence of different Env-gp.

Figure 7:
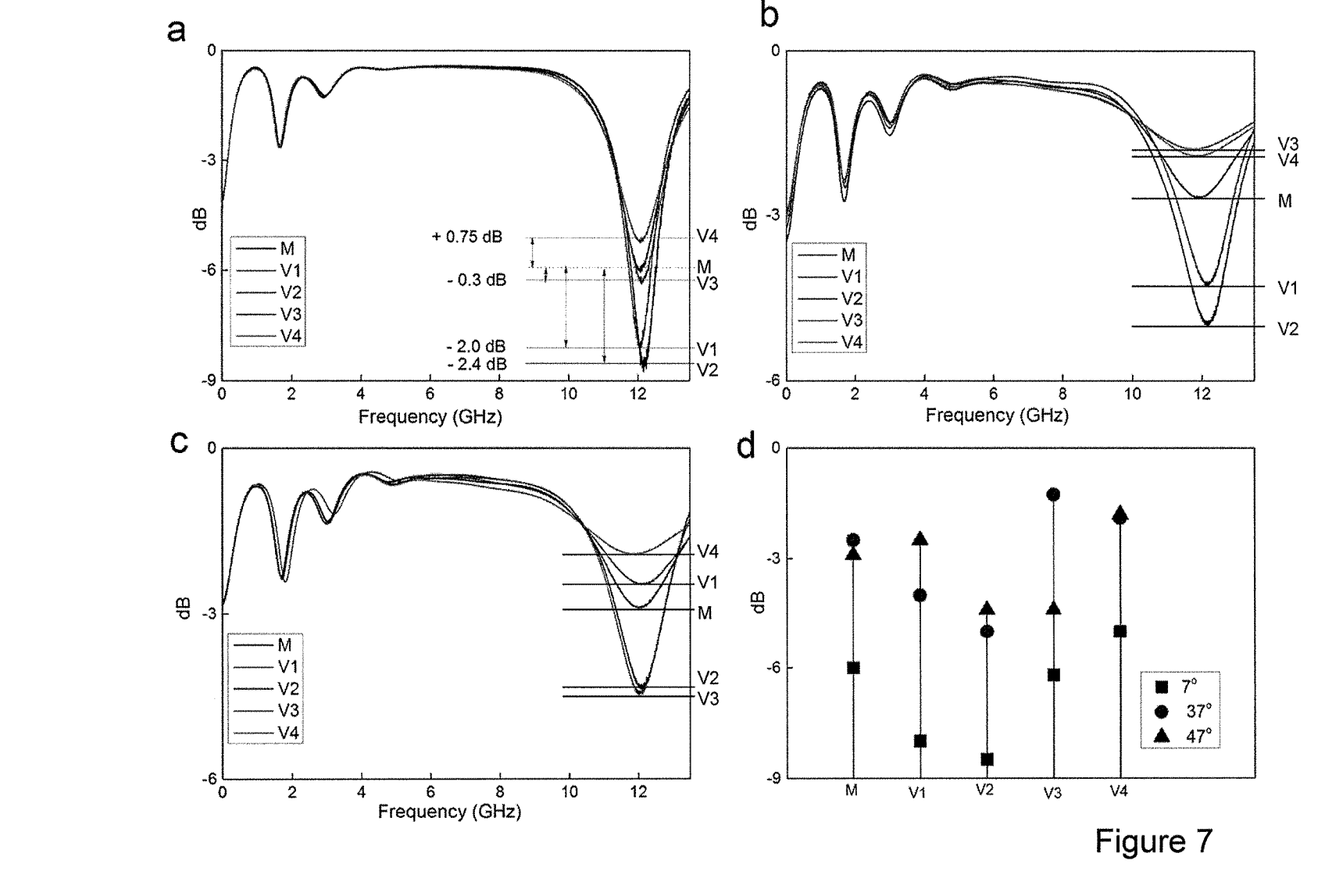
FIGS. 7a, 7b and 7c show frequency responses of several types of viruses at 7° C., 37° C. and 47° C. respectively.
FIG. 7d shows a comparison of the frequency responses of these viruses at these temperatures.

As will be understood by a person of ordinary skill, profiles similar to those in FIG. 7 can be drawn up for phase shifts made to RF signals passing through the lab-on-chip device with virus deposited therein in the aforementioned frequency range (10 MHz to 13.6 GHz). The phase shift characteristics can also be used to identify a type of virus.

Figure 8:
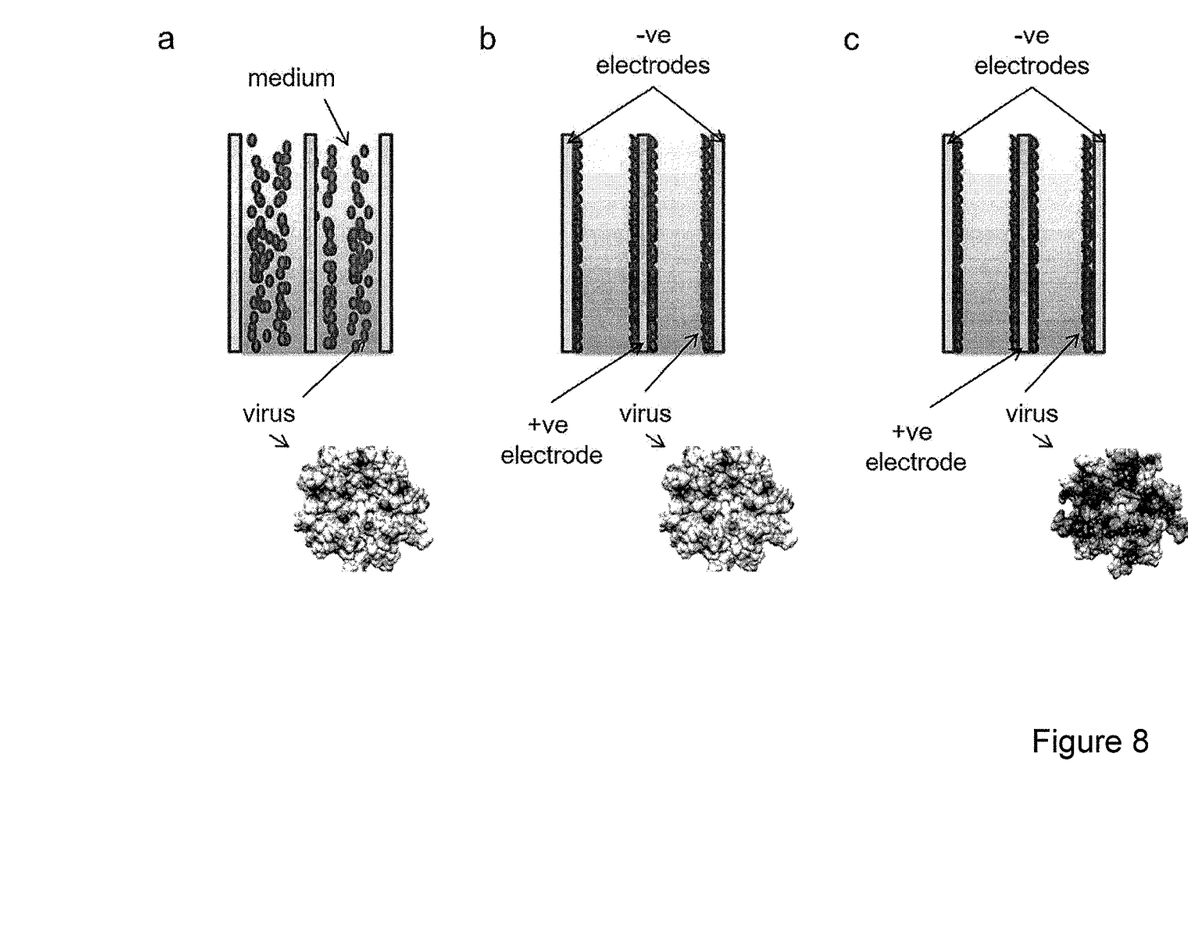
FIGS. 8a, 8b and 8c together illustrate effect of radio frequency signals and temperature on virus.

FIG. 8 illustrates the temperature effect on the viruses. FIG. 8a shows the viral particles distribution within the medium when there is no applied RF field. As depicted in FIG. 8b, with RF propagating through the particles, the particles get polarized and align at the device electrodes based on their polarity—negative particles are attracted to the positive electrode, and the positive particles are attracted to the negative electrodes. The virus particles initially possess high conductivity. However, with an increased temperature, their morphology changes and they become more agitated and electrically more resistive as shown in FIG. 8c. Since different viral particles were produced following the DNA transfection into 293T cells, which allowed them to have a common lipid bilayer in addition to being pesudotyped by a common Env-gp as explained earlier. Therefore, the polarization of these viral particles at different temperatures can consequently be attributed specifically to each viral particle used for the study.

The above demonstrates the use of high frequency measurements at different temperatures for detection of retroviruses and lentiviruses in suspended DMEM based solutions. Among the label-free methods that may be used to directly detect viruses, the method according to embodiments of the present invention provides a combination of advantages, such as high sensitivity, quick response, low cost, high throughput, and ease of use.

Figure 9:
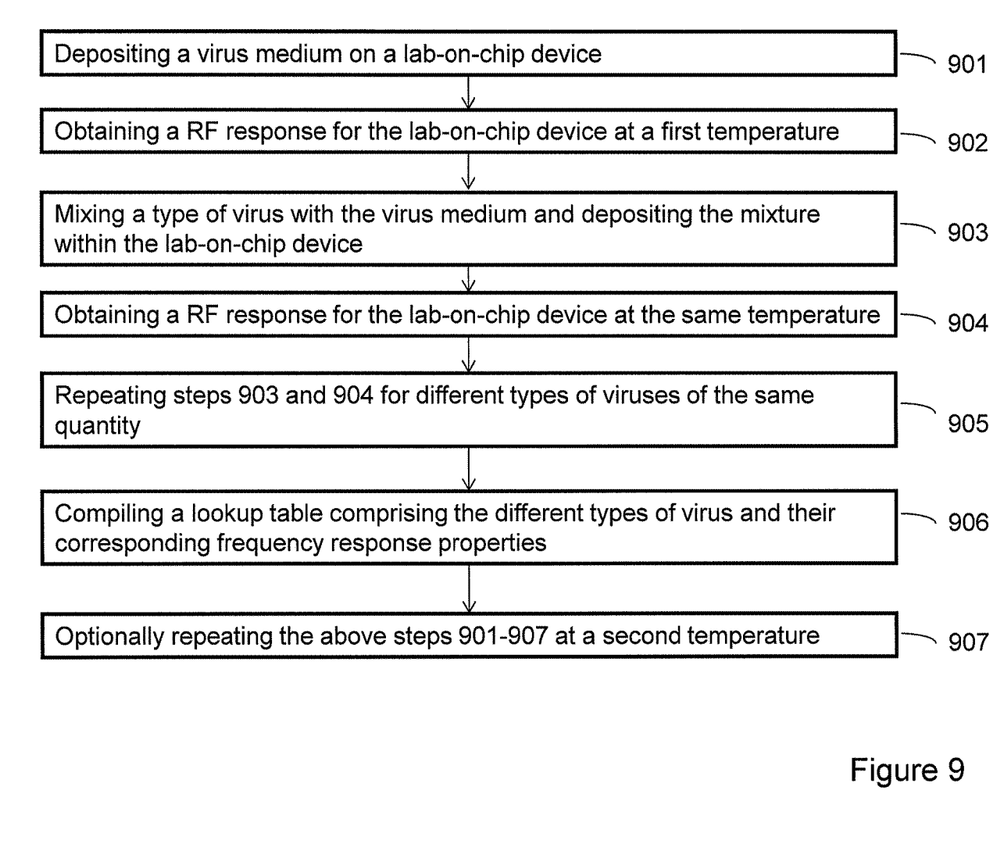
FIG. 9 shows a method for compiling a lookup table according to some embodiments of the present invention.

FIG. 9 illustrates a method for obtaining a lookup table, which can be used to identify several types of viruses according to an embodiment of the present invention.

Figure 4:
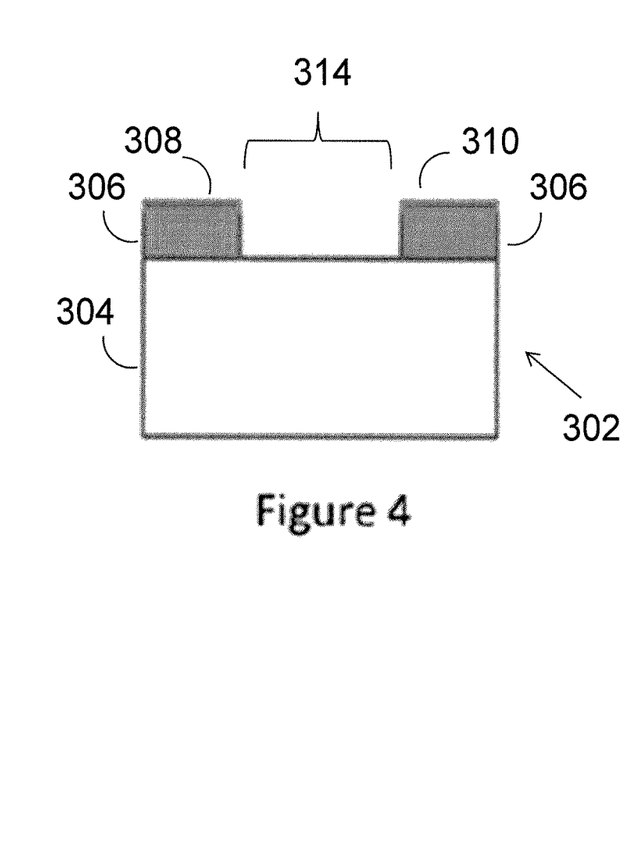
FIG. 4 shows a cross-sectional view of a resonator used in a second embodiment of the invention.
Figure 5:
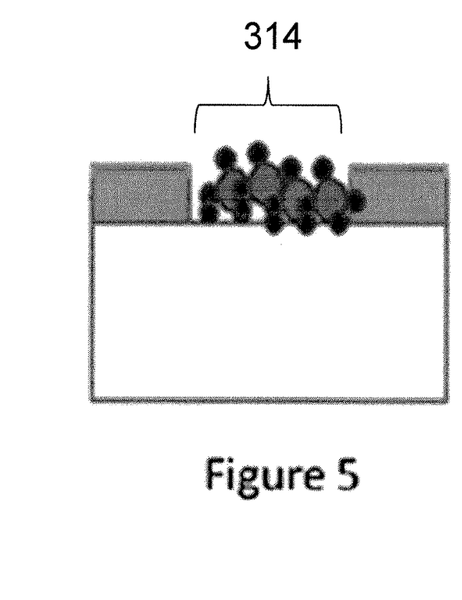
FIG. 5 shows a cross-sectional view of the resonator used in the second embodiment of the invention with virus deposited therein.

In step 901, a virus medium, such as DMEM, is deposited on a lab-on-chip device, such as a device shown in FIG. 1 or 4. In step 902, a RF response of the lab-on-chip device with the medium deposited therein is obtained at a first temperature, e.g. 37° C., using a Vector Network Analyzer. The measurements of the response, including a magnitude of the RF response at a resonance frequency of the device are recorded.

In step 903, a type of virus is mixed with the virus medium and the mixture is deposited within the lab-on-chip device. In step 904, a RF response is obtained for the lab-on-chip device with the mixture deposited therein at the same temperature, namely 37° C. in this embodiment. Measured parameters of the RF response, including a magnitude of the RF response at the resonance frequency, are recorded.

In step 905, steps 903 and 904 are repeated for different types of viruses at the first temperature, namely 37° C. in this embodiment. An equal amount of virus is used for the frequency response analysis for the different types of viruses.

In step 906, a lookup table is compiled. The table comprises the different types of viruses and their corresponding frequency response properties, including magnitudes (and/or changes in signal magnitudes compared to the medium response) at their resonance frequencies at the first temperature (37° C. in this embodiment). The following shows an example of a format of the lookup table.

TABLE 1

| Virus type | 1) Dielectric constant | 2) Phase | 3) Resonance frequency | 4) Magnitude of frequency response at the resonance frequency (at 37° C.) | 5) Change in magnitude at the resonance frequency compared to the medium response (at 37° C.) |
|---|---|---|---|---|---|
| HIV | | | | | |
| FIV | | | | | |
| MMTV | | | | | |
| MPMV | | | | | |

In an optional step 907, steps 901-906 are repeated at a second temperature, e.g. 47° C. For each type of virus, the difference of signal magnitudes at the resonance frequency at the first and the second temperatures are calculated and recorded the change in the lookup table.

Figure 10:
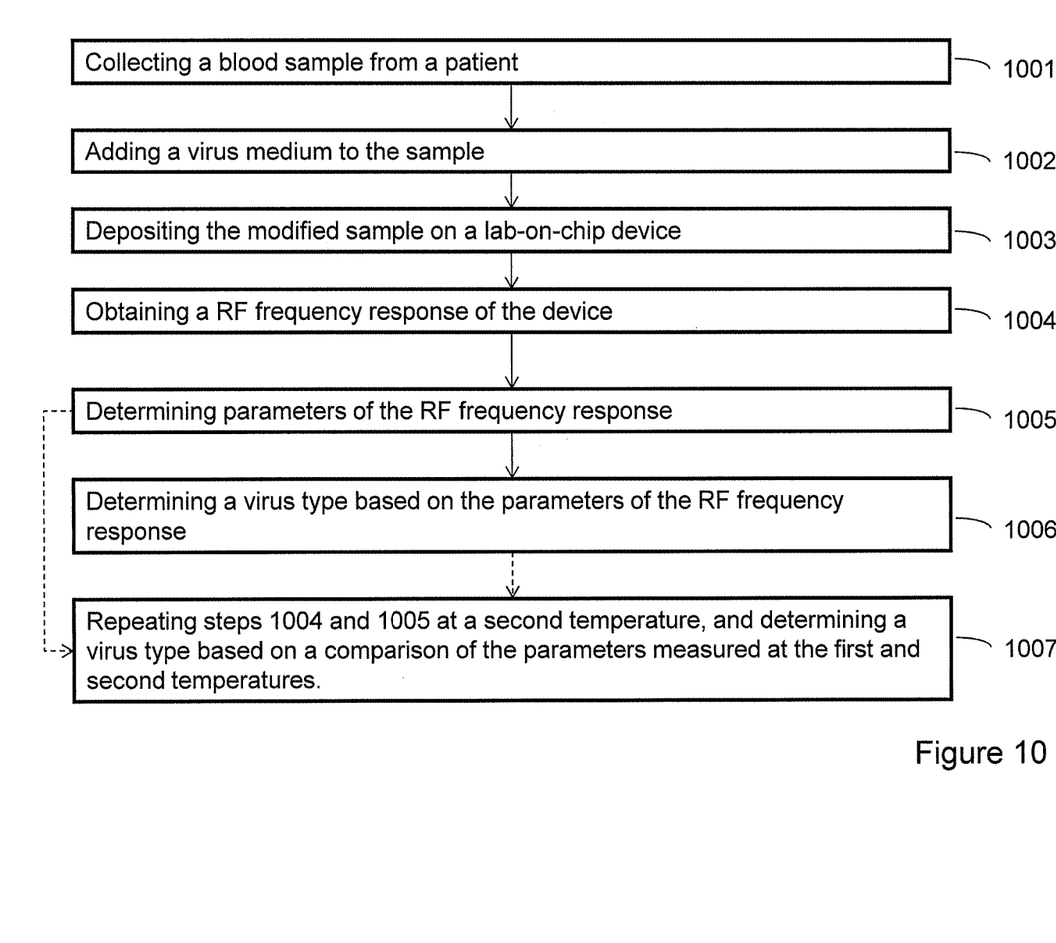
FIG. 10 shows a method for determining a type of virus according to some embodiments of the present invention.

FIG. 10 illustrates a process of identifying a virus to be a particular type of virus according to one embodiment of the present invention.

In step 1001, a specimen, such as a blood sample, is obtained. This may be obtained from a patient. In step 1002, a virus medium, e.g. DMEM or other functionalized nanoparticles, is added to the specimen. The virus medium helps increase sensitivity of the measurements and helps attaching the viral particles to the nanoparticles.

In step 1003, the modified specimen is deposited on a resonator, such as the lab-on-chip device illustrated in FIG. 1 or 4. In step 1004, a RF frequency response is measured using, e.g. a Vector Network Analyser, at the first temperature.

In step 1005, the measurement results are used to determine RF frequency response parameters, such as a frequency shift and magnitude at the resonance frequency. In step 1006, a virus type is determined by checking at least one of the determined parameters against data in a pre-defined lookup table, e.g. a table obtained in step 906. For example, a magnitude at the resonance frequency of the device with virus deposited therein can be checked against the data in column 4 of table 1, and a type of virus can be determined if the magnitude corresponds to the data of any one of HIV, FIV, MMTV and MPMV in column 4 of table 1. This determination may be performed manually or automatically by a computer software program run on a computer.

Step 1007 can be used as an alternative way of identifying a type of virus or an additional step to confirm the virus type determined in step 1006. In step 1007, steps 1004 and 1005 are repeated at a second temperature, e.g. 47° C. The change in signal magnitude at the resonance frequency when the temperature is changed from the first temperature to the second temperature is determined. By checking the change of magnitude at the resonance frequency against data in a pre-defined look-up table, e.g. data in column 4 and/or column 5 of table 1 obtained in step 907, it can be determined whether the virus is HIV, FIV, MMTV or MPMV. This determination may be performed manually or automatically by a computer software program run on a computer.

Methods according to various embodiments of the present invention may be performed by using a Vector Network Analyzer to measure parameters of the frequency responses of a lab-on-chip based resonator with virus deposited within. As set out above, a user may manually check the measured parameters against a pre-defined look-up table compiled according to method illustrated in FIG. 9. Alternatively, data of the look-up table may be stored in a memory, and a processor may be used to check the measured parameters of the frequency response against the stored data of the look-up table. The processor and the memory may be provided in a separate device, which operatively connects to the VNA. Alternatively, the VNA, the processor, and the memory may be integrated into a single device, which may be a portable device.

The advantages of adopting the RF technology and nanotechnologies in virus detection include avoiding the use of biomarker and utilize the change in the frequency response caused by the present of the virus inside a sample, such as human blood. The RF detection based methodology according to various embodiments of the present invention provide following: 1) quick and fast initial screening: the time for determining the presence of virus being less than 1 minute; 2) the possibility of characterizing virus using a living cell rather than the conventional way of using dead cell; 3) quick identification of a type of virus after the initial screening by processing the RF response, extracting certain parameters and comparing with a Lookup table for virus properties using. e.g. a computer based software program; 4) Suitability for Emergency cases: fast and quick check; 5) compact size; and 6) ability to detect a variety of virus.

The present invention is not to be limited in scope by the specific aspects and embodiments described herein. Indeed, various modifications of the invention in addition to those described herein will become apparent to those skilled in the art from the foregoing description and accompanying figures. Such modifications are intended to fall within the scope of the appended claims. Moreover, all aspects and embodiments described herein are considered to be broadly applicable and combinable with any and all other consistent aspects and embodiments, as appropriate.

The invention claimed is:

1. A method comprising:
obtaining at a first temperature a radio frequency response of a lab-on-chip based resonator with a virus deposited within a recess of the resonator,
determining at the first temperature a first value of at least one parameter of the radio frequency response,
obtaining, at a second temperature, a radio frequency response of the resonator with the virus deposited within the resonator;
determining at the second temperature a second value of the at least one parameter; and
identifying a type of the virus or a group to which the virus belongs based on a comparison between the first value and the second value,
wherein the first temperature is 37° C., and the second temperature is 47° C.

2. The method of claim 1, wherein the at least one parameter comprises an amplitude or a change of amplitude at a resonance frequency of the resonator with the virus deposited therein.

3. The method of claim 2, wherein determining the amplitude at the resonance frequency of the resonator at the first and the second temperatures is performed by a Vector Network Analyser.

4. The method of claim 1, further comprising:
measuring at the first temperature the first value of the at least one parameter when a different types of virus is deposited within the resonator,
compiling a lookup table containing at least the measured first value obtained for the virus and the different type of virus.

5. The method of claim 1, wherein the lab-on-chip based resonator comprises nanotubes, and the virus is deposited between gaps of the nanotubes.

6. The method of claim 1, wherein the virus is mixed with functionalized nanoparticles when being deposited.

7. The method of claim 6, wherein the functionalized nanoparticles are antibodies and/or quantum dots.

8. The method of claim 1, wherein obtaining a radio frequency response of the resonator is performed by a Vector Network Analyser (VNA).

9. The method of claim 1, wherein the at least one parameter comprises at least one of: a resonance frequency, a change in resonance frequency, a phase at a particular frequency, and a phase shift at a particular frequency of the frequency response.

10. The method of claim 1, wherein the virus identified is HIV if the first value and the second value are substantially identical, wherein the at least one parameter is a magnitude of the frequency response at the resonance frequency.

11. An apparatus comprising:
a device configured to obtain, at a first temperature and a second temperature, a radio frequency response of a lab-on-chip based resonator with a virus deposited within a recess of the resonator,
a device configured to determine a first value of at least one parameter of the radio frequency response obtained at the first temperature and to determine a second value of the at least one parameter of the radio frequency response obtained at the second temperature,
at least one processor and at least one memory for storing the first and second value, the processor causing the apparatus to identify a type of the virus or a group to which the virus belongs based on a comparison between the first and second values of the at least one parameter, wherein the first temperature is 37° C., and the second temperature is 47° C.

12. The apparatus of claim 11, wherein the at least one parameter is a magnitude or a change of magnitude at a resonance frequency of the resonator with the virus deposited therein.

13. The apparatus of claim 11, wherein the device for obtaining the radio frequency response of the resonator is a Vector Network Analyser (VNA).

14. The apparatus of claim 11, wherein the first value and the second value are substantially identical and the virus is identified to be HIV.

15. The apparatus of claim 11, wherein the at least one parameter comprises at least one of: a resonance frequency, a change in resonance frequency, a phase at a particular frequency, and a phase shift at a particular frequency of the frequency response.

16. The apparatus of claim 11, wherein the at least one processor and the at least one memory are configured to cause the apparatus to identify the type of the virus or the group to which the virus belongs based on the first and second values of the at least one parameter and data stored in the memory.

* * * * *